US006416474B1

(12) United States Patent
Penner et al.

(10) Patent No.: US 6,416,474 B1
(45) Date of Patent: Jul. 9, 2002

(54) SYSTEMS AND METHODS FOR DEPLOYING A BIOSENSOR IN CONJUNCTION WITH A PROSTHESIS

(75) Inventors: Avi Penner, Tel Aviv; Lone Wolinsky, Ramat Gan, both of (IL)

(73) Assignee: Ramon Medical Technologies Ltd., Caesarea (IL)

( * ) Notice: Subject to any disclaimer, the term of this patent is extended or adjusted under 35 U.S.C. 154(b) by 0 days.

(21) Appl. No.: 09/522,370

(22) Filed: Mar. 10, 2000

(51) Int. Cl.[7] ................................................. A61B 5/00
(52) U.S. Cl. ........................ 600/309; 600/325; 600/485; 604/96.01; 604/103.02
(58) Field of Search .................................. 600/309, 325, 600/327, 332, 337, 339, 341–342, 360, 372, 373, 420–424, 431–435, 462, 466–470, 478, 505, 581, 485; 623/1.1–1.54; 606/108; 604/96.01, 103.02

(56) References Cited

U.S. PATENT DOCUMENTS

| 5,855,563 | A | * | 1/1999 | Kaplan et al. ............... 604/509 |
| 5,967,986 | A | * | 10/1999 | Cimochowski et al. ..... 600/454 |
| 6,097,984 | A | * | 8/2000 | Douglas ....................... 607/40 |
| 6,159,156 | A | * | 12/2000 | Van Bockel ................. 600/485 |
| 6,179,858 | B1 | * | 1/2001 | Squire et al. ............... 606/198 |

FOREIGN PATENT DOCUMENTS

| EP | 0928598 A2 | * | 7/1999 |
| WO | WO 83/03348 A1 | | 10/1983 |

OTHER PUBLICATIONS

Webster's II new Riverside University Dictionary, Riverside Publishing Company, 1994, pp. 421 and 625.*

* cited by examiner

Primary Examiner—Eric F. Winakur
Assistant Examiner—Mathew Kremer
(74) Attorney, Agent, or Firm—Lyon & Lyon LLP

(57) ABSTRACT

A biosensor for monitoring pressure or other physical parameters at an aneurysm site is mountable to a tubular prosthesis that is expandable between contracted and enlarged conditions. A loop, having the biosensor attached thereto, is securable around the prosthesis. An apparatus is used to deliver the loop to an aneurysm site that includes a catheter having a connector on its distal end for detachably securing the loop thereto. The prosthesis is advanced in a contracted state to the aneurysm, and the apparatus, with the loop connected thereto, is advanced to the aneurysm site. The loop and the prosthesis are positioned coaxially with respect to one another, and the prosthesis is expanded towards its enlarged condition, thereby engaging the loop around the prosthesis and engaging the prosthesis with a wall of the blood vessel at the treatment site.

41 Claims, 4 Drawing Sheets

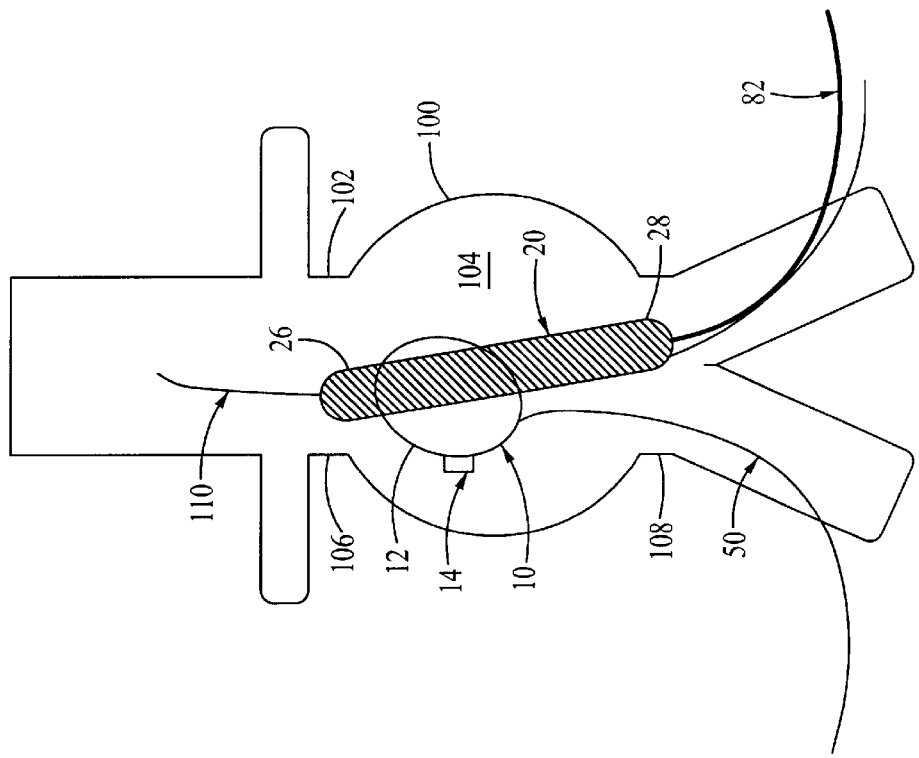
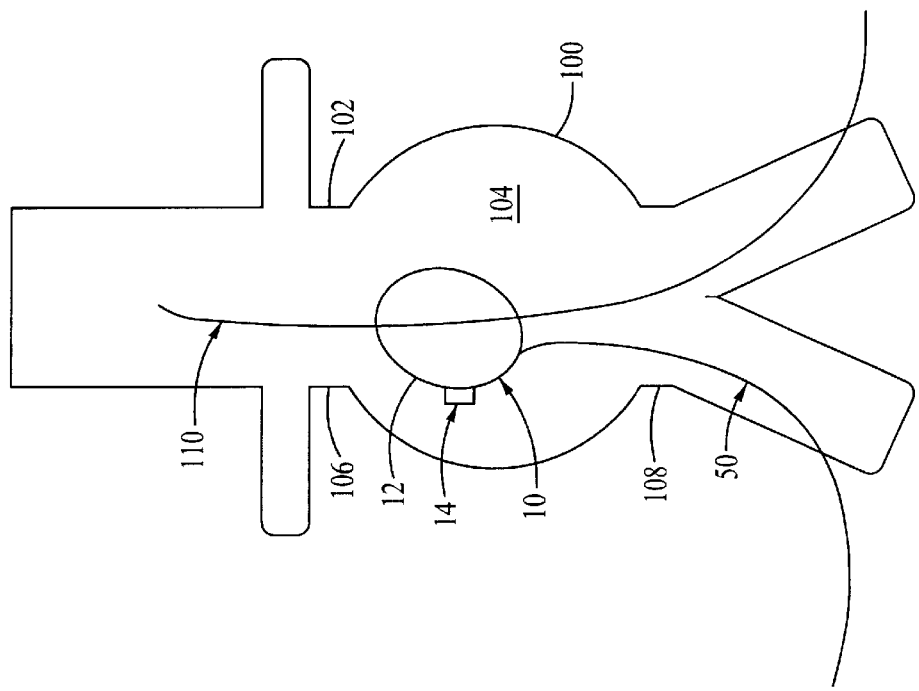

SYSTEMS AND METHODS FOR DEPLOYING A BIOSENSOR IN CONJUNCTION WITH A PROSTHESIS

FIELD OF THE INVENTION

The present invention relates generally to implantable medical devices for monitoring internal physiological conditions of a patient, and, more particularly, to a biosensor that is attachable to a prosthesis for remotely monitoring physiological conditions of a patient, such as pressure within an aneurysm cavity across which a prosthesis is implanted.

BACKGROUND

An aneurysm is a weakening of a wall of a blood vessel that generally results in a ballooning of the wall, and, if left untreated, may result in a rupture that may seriously threaten the life of a patient. The weakening of the wall may be due to injury, infection, or other conditions, such as a congenital defect in the arterial connective tissue. Common forms of such an aneurysm include an abdominal aortic aneurysm ("AAA"), an iliac aneurysm, a bifurcated aneurysm of the abdominal aorta and one or both of the iliac arteries, and a thoracic aortic aneurysm.

To treat a patient suffering from an aneurysm, a tubular prosthetic graft may be implanted across the aneurysm using an open surgical technique to substantially isolate the weakened region of the vessel from adjacent healthy regions. For example, the vessel wall may be cut longitudinally along the vessel wall, the graft inserted and anastomosed coaxially within the vessel as an internal replacement for the diseased segment, and then the longitudinal cut may be sutured closed. Alternatively, opposite ends of a prosthetic graft may be sutured to a vessel on either side of the weakened region to form a bypass conduit around the diseased segment. Such surgical approaches, however, may involve extensive recovery times, may be complicated because of the difficulties in suturing the graft to the vessel, and/or may be unsuitable for many at-risk patients because of the high mortality and morbidity rates associated with a surgical intervention of this magnitude.

As an alternative to open surgery, endolumenal stent graft implantation has been suggested. An endolumenal stent graft generally includes a vascular graft and a support structure, such as a self-expanding or balloon-expandable stent, that may engage each end of the graft or may extend along all or a portion of a length of the graft. The stent graft may be introduced percutaneously into the patient's vasculature in a reduced profile, for example, on or in a delivery catheter. The stent graft may be advanced to a treatment site, such as a damaged segment of the abdominal aorta, and placed across the treatment site. The support structure may then be radially expanded, anchoring the graft to the healthy regions of the vessel adjacent the damaged segment, and substantially sealing the aneurysm from the rest of the circulatory system. As a result, pressure within the isolated aneurysmal sac may be reduced, thereby reducing stress or "endotension" on the weakened wall of the vessel. Endotension is a physical parameter that may indicate the likelihood of an aneurysm rupturing, and is generally defined in terms of the internal pressure within the aneurysm, the aneurysm diameter and vessel wall thickness.

One potential complication that may occur after a stent graft is implanted is the formation of an endoleak. Endoleaks may be divided into four categories: leakage due to improper sealing of the graft against the vessel wall (Type I), blood flow into the aneurysmal sac through bypass arteries (Type II), leakage due to mechanical failure of the graft system (Type III), and leakage through the graft due to the porosity of the graft material (Type IV).

If fluid leaks into the aneurysmal sac, it may increase the pressure or endotension within the aneurysm, possibly resulting in an aneurysmal rupture. To substantially reduce the risk of this occurring, early detection of endoleaks or endotension may be important. With early detection, the pressure within the aneurysmal sac may be reduced by subsequent endovascular treatment (for example, further expansion of the stent graft support structure, or additional stent graft implantation to improve sealing), or, if necessary, surgical intervention.

Currently, contrast-enhanced computerized tomography (CT) is often used to detect endoleaks, which relies on x-ray imaging of an abdominal region after injection of a contrast media. If an endoleak is present, the aneurysmal sac may fill with contrast media and the endoleak may then be identified by the CT scan. Although CT scans are considered a reliable method for detecting endoleaks, they require an experienced operator and an expensive apparatus, placing significant financial constraints on its frequency of use. In addition, a CT scan procedure exposes the patient to x-ray radiation, and thus may only be recommended every 3 to 6 months following stent graft implantation. Finally, because CT scans only detect actual leakage and not pressure within the aneurysm, they may not detect small leaks that may cause slow, but potentially dangerous, pressurization within the aneurysm.

As an alternative to CT scans, ultrasound imaging may be used to detect endoleaks. Ultrasound imaging uses a simpler apparatus, resulting in a potential cost savings over CT scanning, and does not involve the use of ionizing radiation and its associated risks. The quality of ultrasound imaging, however, may be more operator dependent, and therefore may be less reliable than CT scans.

Accordingly, it is believed that a system and method for monitoring internal pressure within an aneurysmal sac may be considered useful.

SUMMARY OF THE INVENTION

The present invention is directed to apparatus and methods for implanting a biosensor, preferably in conjunction with an endoprosthesis, within an abdominal aortic aneurysm or other enlarged or weakened treatment site within a body lumen of a patient.

In accordance with a first aspect of the invention, an apparatus for monitoring a physical parameter at a treatment site within a body lumen is provided. The apparatus includes a tubular prosthesis expandable between a contracted condition for facilitating introduction into the body lumen, and an enlarged condition for contacting a wall of the body lumen at the treatment site. A substantially enclosed loop having a size for substantially securing the loop around the prosthesis in its enlarged condition is provided with a biosensor attached to the loop.

In one preferred embodiment, the loop may be a ring or sleeve formed from a substantially elastic material, the ring or sleeve having a relaxed state having a cross-section smaller than the prosthesis in its enlarged condition. In an alternate preferred embodiment, the loop may be a substantially inelastic, flexible thread having a cross-section similar to the prosthesis in its enlarged condition.

In accordance with another aspect of the invention, an apparatus is provided for delivering the biosensor device to a treatment site within a body lumen. The apparatus includes an elongate member having a proximal end and a distal end adapted for introduction into the body lumen, and a connector located on the distal end of the elongate member for detachably securing the loop to the distal end of the elongate member. Preferably, an actuator is provided on a proximal end of the elongate member for detaching the loop from the connector. In preferred embodiments, the apparatus may also include a sheath slidable over the elongate member or other constraint for constraining the loop to facilitate its introduction into the body lumen.

By way of example, in one preferred embodiment, the connector is a wire having a first end extending from the proximal end of the elongate member, and a second end extending to the distal end of the elongate member. The wire may be intertwined with the loop to thereby substantially secure the loop to the distal end of the elongate member. The actuator preferably is a handle on the first end of the wire for pulling the second end of the wire from the distal end towards the proximal end, thereby releasing the loop therefrom. The loop may include a ring for receiving the wire therethrough.

In accordance with still another aspect of the invention, a delivery device is provided for directing the prosthesis to the treatment site in its contracted condition. The delivery device preferably has a cross-section substantially smaller than a cross-section of the loop, thereby facilitating positioning the loop coaxially with respect to the prosthesis before the prosthesis is deployed from the delivery device.

In accordance with yet another aspect of the invention, a method is provided for implanting a biosensor at a treatment site within a body lumen. In a preferred implementation, a tubular prosthesis is advanced in a contracted state within the body lumen to the treatment site, for example, mounted to a delivery device. A loop is also advanced to the treatment site, the loop including a biosensor attached thereto. Preferably, the loop is detachably connected to a delivery apparatus that is used to advance the loop to the treatment site. The loop may be deployed from a compressed state on the delivery apparatus once advanced to the treatment site, and manipulated to assume an open configuration across the treatment site.

In one preferred embodiment, the loop may be expanded across the treatment site before the prosthesis is advanced to the treatment site, and the prosthesis may be advanced through the loop upon advancement of the prosthesis to the treatment site. Alternatively, the loop may be advanced coaxially over the delivery device to the treatment site.

Preferably, the loop and the prosthesis may be positioned coaxially with respect to one another at the treatment site. The prosthesis may then be expanded towards an enlarged condition, thereby substantially engaging the loop around the prosthesis and substantially engaging the prosthesis to a wall of the blood vessel at the treatment site. Once the prosthesis is expanded, the loop may be released from the delivery apparatus, and the apparatus withdrawn from the patient. As a result, the biosensor is disposed within an aneurysmal sac at least partially defined by the aneurysm. The biosensor may then be used to remotely monitor the aneurysmal sac to detect pressure, leaks or other desired physical conditions therein.

Other objects and features of the present invention will become apparent from consideration of the following description taken in conjunction with the accompanying drawings.

BRIEF DESCRIPTION OF THE DRAWINGS

FIGS. 4A–4D are cross-sectional views of an abdominal aortic aneurysm, showing the implantation of a stent graft across the aneurysm with a biosensor mounted thereon that is disposed within the aneurysmal sac.

DETAILED DESCRIPTION OF THE PREFERRED EMBODIMENTS

Figure 1:
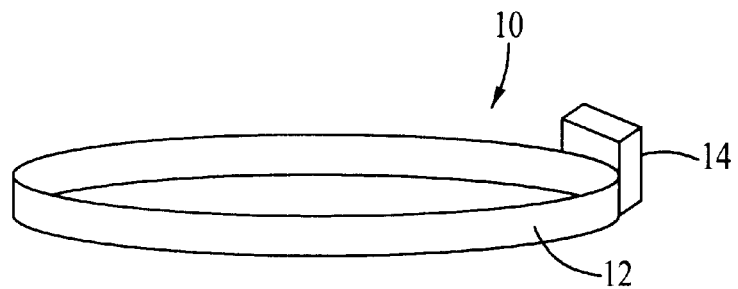
FIG. 1 is a perspective view of a preferred embodiment of a biosensor attached to a flexible band.

Turning now to the drawings, FIG. 1 shows a first preferred embodiment of a biosensor device 10 that includes a loop or lasso 12, preferably a substantially enclosed band of material, to which a biosensor 14 is attached. The biosensor 14 may be attached to the loop 12 by any known method, such as with sutures, adhesives, sonic welding, and the like. The biosensor 14 may be used to remotely measure one or more physical parameters within a patient's body.

For example, the biosensor 14 may be a pressure sensor, a temperature sensor, a pH sensor, a blood sugar sensor, a blood oxygen sensor, a motion sensor, a flow sensor, a velocity sensor, an acceleration sensor, a force sensor, a strain sensor, an acoustics sensor, a moisture sensor, an osmolarity sensor, a light sensor, a turbidity sensor, a radiation sensor, an electromagnetic field sensor, a chemical sensor, an ionic sensor, and an enzymatic sensor.

In preferred embodiments, the biosensor 14 employs wireless telemetry to deliver information from the implantation site to an instrument external to the body. Further, the biosensor may or may not require a battery. For example, one preferred biosensor 14 is constructed in accordance with the teachings of U.S. patent application Ser. No. 09/303,644, which is fully incorporated by reference for all that it teaches and discloses. As taught therein, an acoustic telemetry biosensor includes means for converting acoustic energy received from an externally originated interrogation signal into a current supply for powering one or more sensors embedded in the biosensor for measuring various biological parameters at the implantation site. The biosensor 14 further preferably includes means for modulating the interrogation signal to transmit the measured information external to the body.

In another preferred embodiment, the biosensor 14 is constructed in accordance with the teachings of U.S. Pat. No. 5,704,352, which is also fully incorporated by reference for all that it teaches and discloses. Other biosensor constructions are also possible and will be known to those skilled in the art.

Figures 2A, 2B:
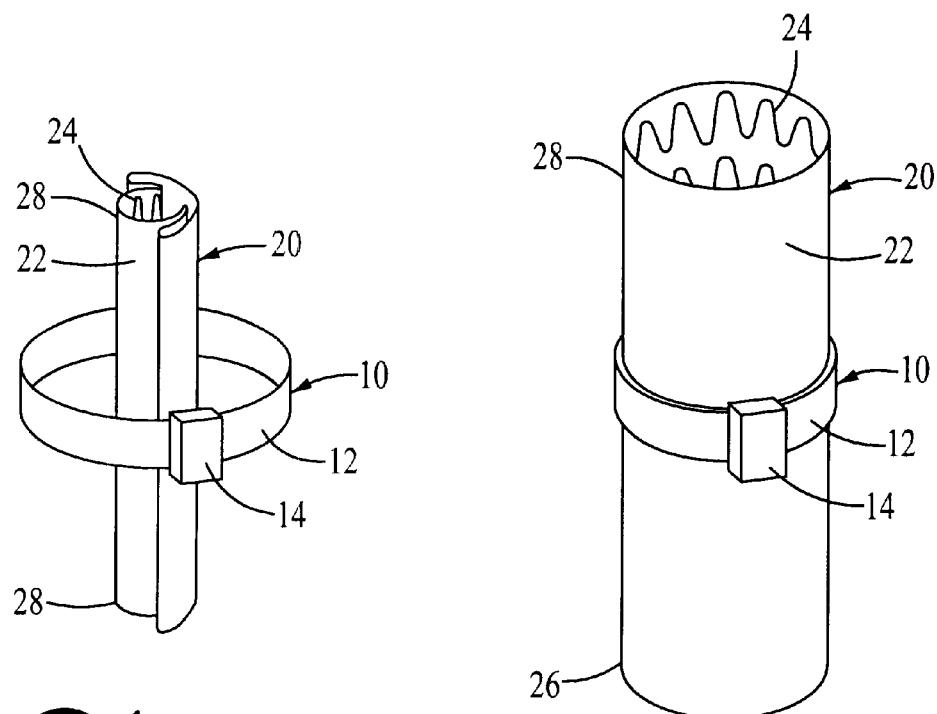
FIGS. 2A and 2B are perspective views of a stent graft in a contracted and an expanded condition, respectively, with the biosensor of FIG. 1 disposed therearound.

Turning to FIGS. 1, 2A, and 2B, the loop 12 has a predetermined cross-section for substantially engaging a prosthesis 20 in its enlarged profile (FIG. 2B). The prosthesis is preferably a stent graft including a tubular prosthetic graft 22 supported by a support structure 24. The graft 22 may be provided from a substantially non-porous biocompatible material, such as Dacron or ePTFE, that is formed into a tubular shape. The material is substantially flexible, thereby allowing the graft 22 to be rolled or folded into a reduced profile, accommodating delivery through tortuous anatomy, and/or facilitating implantation within curved blood vessels.

The support structure 24 is preferably a tubular stent that extends along an inside surface of the graft 22 for substantially the entire length of the graft 22. The support structure 24 may be attached to the graft 22 in a variety of ways, such as by sutures, wires, sonic welding, adhesives, and the like, as is well known in the art.

In an alternative embodiment, the support structure 24 may be attached to an outer surface of the graft (not shown), or may be woven into the graft material (also not shown). In a further alternative, a pair of stents (not shown) may be provided that may be attached to respective end regions of the graft 22, with an intermediate region of the graft 22 being unsupported.

The support structure 24 is radially expandable between a contracted condition (FIG. 2A) for facilitating introduction into a patient's vasculature, and an enlarged condition (FIG. 2B) for substantially engaging the wall of a blood vessel. In one embodiment, the support structure 24 may be a self-expanding stent, i.e., that is biased towards its enlarged condition but may be compressed and/or constrained in its contracted condition during delivery. Alternatively, the support structure 24 may be a plastically-deformable stent, i.e., that remains in its contracted condition until it is forcibly expanded to assume its enlarged condition, for example, using a balloon.

In one preferred embodiment, the loop 12 is formed from a substantially elastic material, such as silicon or polyurethane. The loop 12 preferably has a relaxed state having a cross-section substantially smaller than the prosthesis 20 in its enlarged condition, for example, 25–50% smaller. Preferably, the elastic material has an elasticity such that the loop 12 applies a radially inward pressure against the prosthesis 20 that is sufficiently strong to substantially secure the loop 12 to the prosthesis 20 in its enlarged condition without deforming or damaging the prosthesis 20. For example, the loop 12 may impose a pressure that is less than the anticipated internal pressure experienced within a body lumen, whereby the internal pressure may counteract the inward pressure imposed by the loop 12. Preferably, the loop 12 imposes an inward pressure of between about 5–60 mm Hg against the prosthesis in its enlarged condition.

In alternate preferred embodiments (not shown), the loop 12 may be formed from a substantially inelastic, flexible thread or band of material having a cross-section similar to the prosthesis 20 in its enlarged condition. Preferably, the loop 12 has a cross-section about 5–30 percent larger than a cross-section of the prosthesis 20 in its enlarged condition. Alternatively, the loop 12 may be semi-rigid and may have a "C" shape (not shown) allowing it to be secured around the prosthesis 20 when the prosthesis 20 is expanded. In a still further alternative embodiment, the loop 12 may include an inelastic portion and an elastic portion (not shown).

The loop 12 may be substantially flexible and limp, or alternatively, may be biased to assume a substantially circular, open configuration. For example, the loop 12 may be formed from a shape memory or superelastic alloy, such as a nickel-titanium ("Nitinol™") alloy. Thus, the loop 12 may be compressed, wrapped, or coiled into a compressed state to facilitate its introduction into a patient's vasculature, but may automatically expand to its open configuration upon release at a treatment site where the device 10 is to be implanted.

Figure 3:
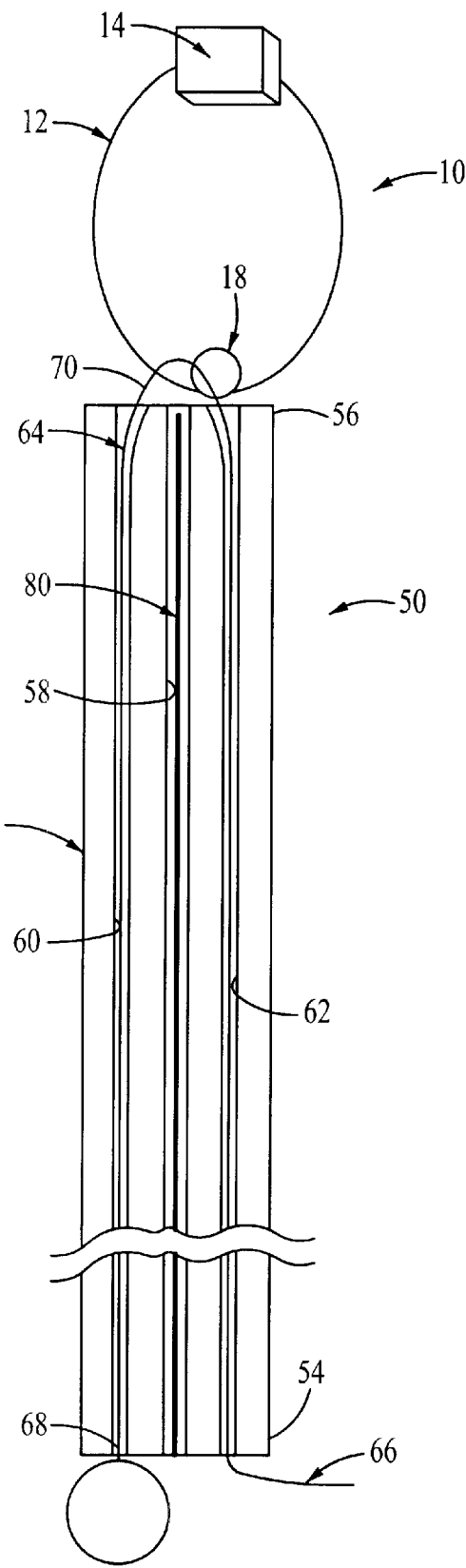
FIG. 3 is a side view of a preferred embodiment of an apparatus for delivering a biosensor device detachably secured to the apparatus by a wire connector.

Turning to FIG. 3, an apparatus 50 is shown for delivering the biosensor device 10 within a body lumen of a patient. The apparatus 50 includes a flexible catheter 52 or other elongate member, having a proximal end 54 and a distal end 56 having a size and shape for facilitating insertion into a patient's vasculature. The catheter 52 may have a guidewire lumen 58 to facilitate advancement of the catheter 52 over a guidewire 80, as is known in the art.

The catheter 52 preferably includes first and second lumens 60, 62 that extend between the proximal and distal ends 54, 56. A wire 64, for example, made of nylon or other flexible, low friction material, may be slidably inserted into the lumens 60, 62 such that first and second ends 66, 68 of the wire 64 extend from the proximal end 54 and an intermediate portion 70 forms a looped connector that extends from the distal end 56. The first end 66 is provided loose, while the second end 68 preferably includes a handle 69.

The loop 12 may be received in the intermediate portion 70 for substantially securing the biosensor device 10 to the distal end 56 of the catheter 52. For example, during assembly, the first end 66 of the wire 64 may be inserted distally into the first lumen 60 from the proximal end 54 of the catheter 52 until it extends from the distal end 56 (not shown). The wire 64 may then be intertwined through the loop 12, preferably through a ring 18 attached to the loop 12, and inserted proximally into the second lumen 62, possibly until the first end 66 extends from the proximal end 56 of the catheter 52. Alternatively, the wire 64 may be intertwined through a hole in the biosensor device 10.

When it is desired to disconnect the biosensor device 10 from the catheter 52, the handle 69 may be pulled until the first end 66 of the wire 64 is pulled from the second lumen 62 and enters the first lumen 60, thereby releasing the loop 12 from the wire 64. Thus, the wire 64 provides a connector for securing the biosensor device 10 to the catheter 52, and the handle 69 provides an actuator for releasing the biosensor device 10 that may be activated from the proximal end 54 of the catheter 52. If additional protection of the biosensor device 10 is desired, an overlying sheath (not shown) may be provided that is slidable over the catheter 52 from the proximal end 54 to the distal end 56. A locking mechanism may be included to prevent the unintentional detachment of the biosensor device 10.

The biosensor device 10 may be received in a lumen of the sheath, for example, simply by advancing the sheath distally over the biosensor device 10, or by compressing the loop 12 and inserting the compressed biosensor device 10 into the sheath.

In an alternative embodiment, the first and second lumens 60, 62 may terminate proximate to the distal end 56, thereby securing the biosensor device 10 to a side region of the catheter 52 (not shown). If desired, the loop 12 may then be wound around the catheter 52 and constrained thereon, for example, by an overlying sheath (not shown).

In a further alternate embodiment, a different connector may be provided on the distal end 56 of the catheter 52, such as a pair of opposing mandibles (not shown) having a slot therebetween for engaging the loop 12, that may be activated by an actuator (not shown) on the proximal end 54 of the catheter 52.

Turning to FIGS. 4A–4D, a method for implanting the biosensor device 10 in conjunction with a prosthesis 20 is shown. In a preferred method, the prosthesis 20 is implanted across an aneurysm 100 in an abdominal aorta 102 of a patient with the biosensor device 10 secured around the prosthesis 20 such that the biosensor 14 is disposed within an aneurysmal sac 104 of the aneurysm 100. Alternatively, the method may be used to treat other enlarged or weakened regions within a blood vessel, for example, an aneurysm within the iliac arteries, the thoracic aorta, the cranial artery, and the like.

As shown in FIG. 4A, a guidewire 110 may be placed across the aneurysm site 100 in a conventional manner, for example, from a peripheral artery, such as the femoral artery (not shown). The biosensor device 10, secured to the distal end 56 of the catheter 52, may be advanced endolumenally to the aneurysm site 100, for example, from the contralateral femoral artery (not shown). Alternatively, the biosensor device 10 may be advanced to the aneurysm site 100 from the same peripheral artery as the guidewire 110 (not shown).

If constrained to the catheter 52, the loop 12 may be released from the constraint (e.g., by withdrawing an overlying sheath) such that it extends substantially transversely across the aneurysm site 100. If the loop 12 is biased to its open configuration, the loop 12 may automatically unfurl or expand after being released to extend across the aneurysm site 100. Otherwise, the loop 12 may be manipulated to properly orient it, for example, under fluoroscopic guidance, which may be facilitated by radiopaque markers (not shown) provided at predetermined locations on the loop 12.

Preferably, the loop 12 is manipulated such that it extends coaxially around the guidewire 110. If the biosensor device 10 is introduced through the ipsilateral artery, the loop 12 may be aligned around the guidewire 110 before the biosensor device 10 is advanced to the aneurysm site 100.

As shown in FIG. 4B, the prosthesis 20, in its contracted condition, may be advanced endolumenally to the aneurysm site 100. For example, the prosthesis 20 may be secured to a delivery device 82, which may include a catheter, a sheath, and/or other conventional device, that may be advanced over the guidewire 100. The prosthesis 20 may be positioned with respect to the loop 12, for example, by advancing the delivery device 82 through the loop 12, and positioning the prosthesis 20 with respect to the aneurysm 100.

This may also be performed under fluoroscopic guidance, with radiopaque markers provided on the delivery device 82 and/or on the prosthesis 20. Preferably, the prosthesis 20 is positioned such that ends 26, 28 of the prosthesis 20 are aligned with the healthy regions 106, 108 of the vessel adjacent to the aneurysm 100. The loop 12 may then be adjusted to position it with respect to the prosthesis 20, i.e., to position the biosensor 14 at a desired location along the length and/or around the outer surface of the prosthesis 20.

Figure 4C:
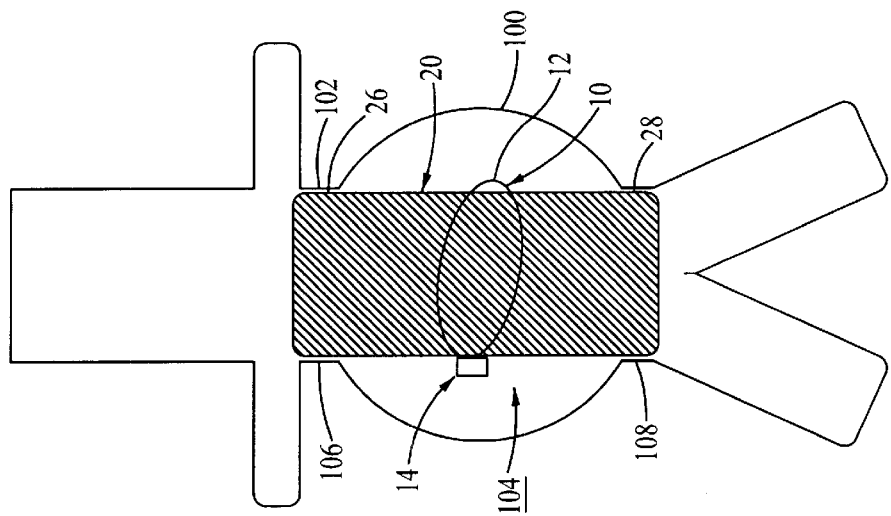

As shown in FIG. 4C, the prosthesis 20 may then be expanded to its enlarged condition, thereby securing the ends 26, 28 to the healthy regions 106, 108 of the vessel, and substantially securing the loop 12 around the prosthesis 20. For example, if the prosthesis 20 includes a self-expanding support structure, the prosthesis 20 may automatically expand upon being released from the delivery device 82. Alternatively, an expandable member, such as a balloon (not shown) on the delivery device 82, may be used to forcibly expand the prosthesis 20, as is known in the art. A final inflation of the balloon may be used to provide a good seal between the distal ends 26, 28 of the prosthesis 20 and the healthy regions 106, 108 of the vessel.

Figure 4D:
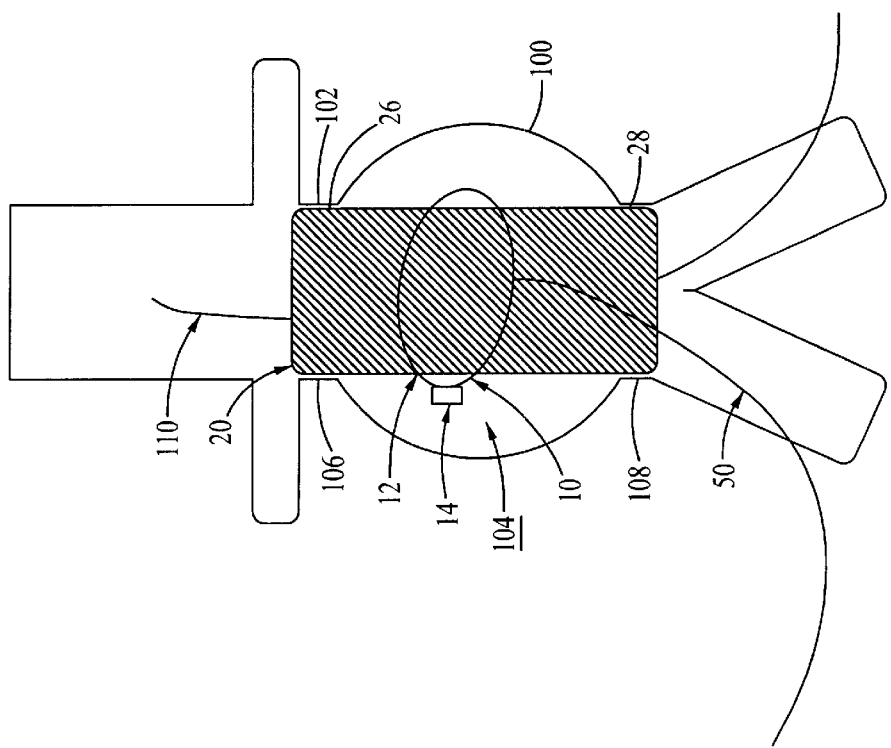

Finally, as shown in FIG. 4D, the biosensor device 10 may be released from the catheter 52, and the catheter 52 and delivery apparatus 82 withdrawn from the patient. Thus, the prosthesis 20 may be used to substantially isolate the aneurysm 100 from the rest of the blood vessel. The biosensor 14 may then be used to monitor physiological conditions of the patient, such as pressure within the aneurysmal sac 102, after implantation of the prosthesis 20. The biosensor 14 may be activated remotely to provide pressure or other data, and thereby facilitate monitoring the condition of an aneurysm to detect early signs of leaks or other potential problems.

In an alternative embodiment, the prosthesis 20, mounted to the delivery device 82 in its contracted condition, may be advanced to the aneurysm site 100 over the guidewire 110 before the biosensor device 10 is introduced therein (not shown). The biosensor device 10 may then be advanced into the aneurysm site 100, as described above, and then positioned around the prosthesis 20 before the prosthesis 20 is expanded towards its enlarged condition.

Alternatively, the loop 12 may be oriented around the delivery device 82 at its proximal end (not shown) and the biosensor device 10 advanced distally over the delivery device 82 using the catheter 52 until the biosensor device 10 is positioned over the prosthesis 20 at the aneurysm site 100. The prosthesis 20 may then be expanded, and the biosensor device 10 released, as described above.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A method for implanting a biosensor at a treatment site within a body lumen of a patient, comprising:
    advancing a tubular prosthesis in a contracted state within the body lumen to the treatment site;
    advancing a substantially enclosed loop to the treatment site, the loop including a biosensor attached thereto;
    positioning the loop and the prosthesis coaxially with respect to one another at the treatment site; and
    expanding the prosthesis towards an enlarged condition, thereby substantially engaging the loop around the prosthesis and substantially engaging the prosthesis with a wall of the blood vessel at the treatment site.

2. The method of claim 1, wherein the loop is advanced to the treatment site within a lumen of a delivery apparatus, the loop being detachably secured to the delivery apparatus.

3. The method of claim 2, further comprising deploying the loop from the delivery apparatus before positioning the loop around the prosthesis.

4. The method of claim 3, further comprising releasing the loop from the delivery apparatus after positioning the loop around the prosthesis.

5. The method of claim 4, wherein the loop is released from the delivery device after the prosthesis is expanded towards its enlarged condition.

6. The method of claim 1, wherein the step of positioning the loop comprises:
    expanding the loop across the treatment site before the prosthesis is advanced to the treatment site; and
    advancing the prosthesis through the loop upon advancement of the prosthesis to the treatment site.

7. The method of claim 1, wherein the prosthesis is advanced to the treatment site mounted to a distal end of a delivery device, and wherein the loop is advanced coaxially over the delivery device to the treatment site.

8. The method of claim 1, wherein the treatment site comprises an aneurysm.

9. The method of claim 8, wherein the biosensor is disposed within an aneurysmal sac at least partially defined by the aneurysm after the prosthesis is expanded to its enlarged condition.

10. An apparatus for delivering a biosensor to a treatment site within a body lumen, comprising:
    a catheter having a proximal end and a distal end adapted for introduction into the body lumen;

an attachment loop having a biosensor attached thereto; and a connector on the distal end of the catheter for detachably securing the attachment loop to the catheter, said connector comprising a wire extending through the catheter, the wire having a distal portion at the distal end of the catheter that is intertwined with the attachment loop to substantially secure the loop to the distal end of the catheter.

11. The apparatus of claim 10, further comprising an actuator on the proximal end of the catheter for detaching the attachment loop from the connector.

12. The apparatus of claim 11, wherein the actuator comprises a handle on a first end of the wire disposed at the proximal end of the catheter, the handle configured for pulling the distal portion of the wire from the distal end of the catheter towards the proximal end, thereby releasing the attachment loop therefrom.

13. The apparatus of claim 10, wherein the attachment loop comprises a ring attached thereto for receiving the wire therethrough.

14. The apparatus of claim 10, further comprising:

a tubular prosthesis expandable between a contracted condition for facilitating introduction into the body lumen, and an enlarged condition for contacting a wall of the body lumen at the treatment site; and a delivery device for directing the prosthesis to the treatment site in its contracted condition, the delivery device having a cross-section substantially smaller than a cross-section of the attachment loop, thereby facilitating positioning the loop coaxially with respect to the prosthesis before the prosthesis is deployed from the delivery device.

15. The apparatus of claim 14, wherein the attachment loop has a size for substantially securing the loop to the prosthesis in its enlarged condition.

16. The apparatus of claim 14, wherein the attachment loop comprises a ring or sleeve formed from a substantially elastic material, the ring or sleeve having a relaxed state having a cross-section smaller than the prosthesis in its enlarged condition.

17. The apparatus of claim 14, wherein the attachment loop comprises a substantially inelastic thread having a cross-section similar to the prosthesis in its enlarged condition.

18. The apparatus of claim 10, further comprising a sheath slidable over the catheter, the sheath being configured for receiving the attachment loop therein.

19. The apparatus of claim 18, wherein the attachment loop is biased to assume an open configuration upon release from the sheath.

20. An apparatus for delivering a biosensor to a treatment site within a body lumen, comprising:

a catheter having a proximal end and a distal end adapted for introduction into the body lumen;

an attachment loop having a biosensor attached thereto, said biosensor extending radially outward from the loop; and a connector on the distal end of the catheter for detachably securing the attachment loop to the catheter.

21. The apparatus of claim 20, further comprising an actuator on the proximal end of the catheter for detaching the attachment loop from the connector.

22. The apparatus of claim 21, wherein the connector comprises a wire extending through the catheter, the wire having a distal portion at the distal end of the catheter that is intertwined with the attachment loop to substantially secure the attachment loop to the distal end of the catheter.

23. The apparatus of claim 22, wherein the actuator comprises a handle on a first end of the wire disposed at the proximal end of the catheter, the handle configured for pulling the distal portion of the wire from the distal end of the catheter towards the proximal end, thereby releasing the attachment loop therefrom.

24. The apparatus of claim 22, wherein the attachment loop comprises a ring attached thereto for receiving the wire therethrough.

25. The apparatus of claim 20, further comprising:

a tubular prosthesis expandable between a contracted condition for facilitating introduction into the body lumen, and an enlarged condition for contacting a wall of the body lumen at the treatment site; and a delivery device for directing the prosthesis to the treatment site in its contracted condition, the delivery device having a cross-section substantially smaller than a cross-section of the attachment loop, thereby facilitating positioning the attachment loop coaxially with respect to the prosthesis before the prosthesis is deployed from the delivery device.

26. The apparatus of claim 25, wherein the attachment loop has a size for substantially securing the attachment loop to the prosthesis in its enlarged condition.

27. The apparatus of claim 25, wherein the attachment loop comprises a ring or sleeve formed from a substantially elastic material, the ring or sleeve having a relaxed state having a cross-section smaller than the prosthesis in its enlarged condition.

28. The apparatus of claim 25, wherein the attachment loop comprises a substantially inelastic thread having a cross-section similar to the prosthesis in its enlarged condition.

29. The apparatus of claim 20, further comprising a sheath slidable over the catheter, the sheath being configured for receiving the attachment loop therein.

30. The apparatus of claim 29, wherein the attachment loop is biased to assume an open configuration upon release from the sheath.

31. An apparatus for monitoring a physical parameter at an aneurysmal site within a blood vessel lumen comprising:

a tubular prosthesis expandable between a contracted condition for facilitating introduction of the prosthesis into the lumen of the blood vessel, and an enlarged condition for contacting a wall of the blood vessel lumen;

a substantially enclosed attachment loop having a size for securing the attachment loop coaxially around the prosthesis in its enlarged condition; and a biosensor attached to the attachment loop and extending radially outward from the attachment loop for positioning the biosensor within an aneurysmal sac.

32. The apparatus of claim 31, wherein the biosensor is a sensor selected from the group consisting of a pressure sensor, a temperature sensor, a pH sensor, a blood sugar sensor, a blood oxygen sensor, a motion sensor, an acceleration sensor, a force sensor, a strain sensor, an acoustics sensor, a moisture sensor, an osmolarity sensor, a light sensor, a turbidity sensor, a radiation sensor, an electromagnetic field sensor, a chemical sensor, an ionic sensor, and an enzymatic sensor.

33. An apparatus for use with a tubular prosthesis in monitoring a physical parameter at a site within a body lumen, comprising:
- a substantially enclosed attachment loop configured for attachment to an outer circumference of the prosthesis; and
- a biosensor attached to the attachment loop, said biosensor extending radially outward from the attachment loop.

34. The apparatus of claim 33, wherein the attachment loop comprises a ring or sleeve formed from a substantially elastic material, the ring or sleeve having a relaxed state having a cross-section smaller than the prosthesis in an enlarged condition.

35. The apparatus of claim 34, wherein the elastic material has an elasticity such that the ring or sleeve applies a radially inward pressure of between about 5–60 mm Hg against the prosthesis in an enlarged condition when the ring or sleeve is substantially secured thereto.

36. The apparatus of claim 33, wherein the attachment loop comprises a substantially inelastic thread having a cross-section similar to the prosthesis in an enlarged condition.

37. The apparatus of claim 36, wherein the thread has a cross-section about 5–30 percent larger than a cross-section of the prosthesis in an enlarged condition.

38. The apparatus of claim 33, wherein the attachment loop is biased to assume a substantially open configuration.

39. The apparatus of claim 33, wherein the attachment loop is compressible to facilitate its insertion into a delivery device.

40. The apparatus of claim 33, wherein the attachment loop comprises a connector thereon for cooperating with a mating connector on a device for delivering the attachment loop within the body lumen.

41. The apparatus of claim 33, wherein the biosensor is a sensor selected from the group consisting of a pressure sensor, a temperature sensor, a pH sensor, a blood sugar sensor, a blood oxygen sensor, a motion sensor, a flow sensor, a velocity sensor, an acceleration sensor, a force sensor, a strain sensor, an acoustics sensor, a moisture sensor, an osmolarity sensor, a light sensor, a turbidity sensor, a radiation sensor, an electromagnetic field sensor, a chemical sensor, an ionic sensor, and an enzymatic sensor.

* * * * *

UNITED STATES PATENT AND TRADEMARK OFFICE
CERTIFICATE OF CORRECTION

PATENT NO.    : 6,416,474 B1
DATED         : July 9, 2002
INVENTOR(S)   : Avi Penner and Lone Wolinsky It is certified that error appears in the above-identified patent and that said Letters Patent is hereby corrected as shown below:

<u>Title page,</u>
Item [73], delete "Ramon Medical Technologies Ltd." and insert -- Remon Medical Technologies Ltd. --

Signed and Sealed this

First Day of October, 2002

*Attest:*

*Attesting Officer*

JAMES E. ROGAN
*Director of the United States Patent and Trademark Office*